(12) United States Patent
Lim et al.

(10) Patent No.: US 8,038,654 B2
(45) Date of Patent: Oct. 18, 2011

(54) SYRINGE HAVING A HINGED NEEDLE SHIELD

(75) Inventors: Kiang Heng Lim, Park Green (SG); Christopher E. Gardner, Warren, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 11/678,739

(22) Filed: Feb. 26, 2007

(65) Prior Publication Data

US 2008/0208138 A1 Aug. 28, 2008

(51) Int. Cl.
*A61M 5/32* (2006.01)
(52) U.S. Cl. .......................................... 604/192
(58) Field of Classification Search ................. 604/181, 604/192, 110, 187, 198
See application file for complete search history.

(56) References Cited

U.S. PATENT DOCUMENTS

| | | | |
|---|---|---|---|
| 1,779,451 A | 10/1930 | Sponsel | |
| 2,004,050 A | 6/1935 | Kerk | |
| 2,473,734 A * | 6/1949 | Smith | 604/192 |
| 2,700,385 A | 1/1955 | Ortiz | |
| 2,836,942 A | 6/1958 | Miskel | |
| 2,854,976 A | 10/1958 | Heydrich | |
| 2,953,243 A | 9/1960 | Roehr | |
| 3,021,942 A | 2/1962 | Hamilton | |
| 3,073,307 A | 1/1963 | Stevens | |
| 3,074,542 A | 1/1963 | Myerson et al. | |
| 3,255,873 A | 6/1966 | Speelman | |
| 3,294,231 A | 12/1966 | Vanderbeck | |
| 3,323,523 A | 6/1967 | Scislowicz et al. | |
| 3,329,146 A | 7/1967 | Waldman, Jr. | |
| 3,333,682 A | 8/1967 | Burke | |
| 3,367,488 A | 2/1968 | Hamilton | |
| 3,485,239 A | 12/1969 | Vanderbeck | |
| 3,537,452 A | 11/1970 | Wilks | |
| 3,610,240 A | 10/1971 | Harautuneian | |
| 3,658,061 A | 4/1972 | Hall | |

(Continued)

FOREIGN PATENT DOCUMENTS

| | | |
|---|---|---|
| GB | 1233302 | 5/1971 |
| GB | 2239604 A | 7/1991 |
| GB | 2239607 A | 7/1991 |

(Continued)

*Primary Examiner* — Theodore Stigell
*Assistant Examiner* — Bradley Osinski
(74) *Attorney, Agent, or Firm* — Jeanne P. Lukasavage; Diehl Servilla LLC

(57) ABSTRACT

A syringe assembly includes a syringe barrel having an elongate body, a tip on its distal end surrounded by a barrel collar. A needle assembly includes a needle cannula attached to a hub having a cavity in its open proximal end. The hub is attached to the barrel with the barrel tip in the hub cavity. A plunger having a stopper positioned in fluid tight engagement on the inside of the barrel. A collar is rotatably connected to the outside surface of the barrel collar. An elongate needle shield is hingedly connected to the collar. The needle shield includes two side walls defining a longitudinal opening and a recess. A needle shield is capable of pivoting about the collar from an open position to a closed position wherein the distal end of the needle cannula is in the recess of the needle shield. Structure is provided to lock the needle shield to the collar and to trap the needle cannula in the needle shield when the needle shield is in the closed position. Structure is provided to prevent over-rotation of the needle shield past the needle protecting position and to guide a needle cannula into the recess of the needle shield. An over-center hinge facilitates moving the needle shield to the closed position.

20 Claims, 14 Drawing Sheets

U.S. PATENT DOCUMENTS

| | | |
|---|---|---|
| 3,828,775 A | 8/1974 | Armel |
| 3,890,971 A | 6/1975 | Leeson et al. |
| 3,904,033 A | 9/1975 | Haerr |
| 3,934,722 A | 1/1976 | Goldberg |
| 3,968,876 A | 7/1976 | Brookfield |
| 4,113,090 A | 9/1978 | Carstens |
| 4,139,009 A | 2/1979 | Alvarez |
| 4,175,008 A | 11/1979 | White |
| 4,300,678 A | 11/1981 | Gyure et al. |
| RE31,086 E | 11/1982 | Johnson, Jr. et al. |
| 4,375,849 A | 3/1983 | Hanifl |
| 4,430,082 A | 2/1984 | Schwabacher |
| 4,592,744 A | 6/1986 | Jagger et al. |
| 4,634,428 A | 1/1987 | Cuu |
| 4,643,722 A | 2/1987 | Smith, Jr. |
| 4,659,330 A | 4/1987 | Nelson et al. |
| 4,664,249 A | 5/1987 | Gherardi |
| 4,664,259 A | 5/1987 | Landis |
| 4,664,654 A | 5/1987 | Strauss |
| 4,671,408 A | 6/1987 | Raines et al. |
| 4,681,567 A | 7/1987 | Masters et al. |
| 4,695,274 A | 9/1987 | Fox |
| 4,702,738 A | 10/1987 | Spencer |
| 4,723,943 A | 2/1988 | Spencer |
| 4,728,320 A | 3/1988 | Chen |
| 4,728,321 A | 3/1988 | Chen |
| 4,731,059 A | 3/1988 | Wanderer et al. |
| 4,735,311 A | 4/1988 | Lowe et al. |
| 4,735,618 A | 4/1988 | Hagen |
| 4,737,144 A | 4/1988 | Choksi |
| 4,738,663 A | 4/1988 | Bogan |
| 4,743,233 A | 5/1988 | Schneider |
| 4,746,008 A | 5/1988 | Heverly et al. |
| 4,747,836 A | 5/1988 | Luther |
| 4,747,837 A | 5/1988 | Hauck |
| 4,772,272 A | 9/1988 | McFarland |
| 4,778,453 A | 10/1988 | Lopez |
| 4,781,697 A | 11/1988 | Slaughter |
| 4,782,841 A | 11/1988 | Lopez |
| 4,790,828 A | 12/1988 | Dombrowski et al. |
| 4,793,484 A | 12/1988 | Schoettle |
| 4,795,432 A | 1/1989 | Karczmer |
| 4,795,443 A | 1/1989 | Permenter et al. |
| 4,801,295 A | 1/1989 | Spencer |
| 4,804,372 A | 2/1989 | Laico et al. |
| 4,813,426 A | 3/1989 | Haber et al. |
| 4,816,022 A | 3/1989 | Poncy |
| 4,816,024 A | 3/1989 | Sitar et al. |
| 4,819,659 A | 4/1989 | Sitar |
| 4,820,277 A | 4/1989 | Norelli |
| 4,826,490 A | 5/1989 | Byrne et al. |
| 4,826,491 A | 5/1989 | Schramm |
| 4,838,871 A | 6/1989 | Luther |
| 4,842,587 A | 6/1989 | Poncy |
| 4,846,796 A | 7/1989 | Carrell et al. |
| 4,850,968 A | 7/1989 | Romano |
| 4,850,976 A | 7/1989 | Heinrich et al. |
| 4,858,607 A | 8/1989 | Jordan et al. |
| 4,863,434 A | 9/1989 | Bayless |
| 4,863,435 A | 9/1989 | Sturman et al. |
| 4,863,436 A | 9/1989 | Glick |
| 4,867,746 A | 9/1989 | Dufresne |
| 4,872,552 A | 10/1989 | Unger |
| 4,874,383 A | 10/1989 | McNaughton |
| 4,874,384 A | 10/1989 | Nunez |
| 4,883,469 A | 11/1989 | Glazier |
| 4,886,503 A | 12/1989 | Miller |
| 4,888,001 A | 12/1989 | Schoenberg |
| 4,892,107 A | 1/1990 | Haber |
| 4,892,521 A | 1/1990 | Laico et al. |
| 4,900,309 A | 2/1990 | Netherton et al. |
| 4,909,485 A | 3/1990 | Norelli |
| 4,909,792 A | 3/1990 | Norelli |
| 4,921,096 A | 5/1990 | McFarlane |
| 4,927,018 A | 5/1990 | Yang et al. |
| 4,944,397 A | 7/1990 | Miller |
| 4,944,731 A | 7/1990 | Cole |
| 4,966,591 A | 10/1990 | Yuen |
| 4,976,699 A | 12/1990 | Gold |
| 4,982,842 A | 1/1991 | Hollister |
| 5,011,475 A | 4/1991 | Olson |
| 5,011,479 A | 4/1991 | Le et al. |
| 5,055,102 A | 10/1991 | Sitnik |
| 5,078,693 A | 1/1992 | Shine |
| 5,116,325 A | 5/1992 | Paterson |
| 5,135,509 A | 8/1992 | Olliffe |
| 5,139,489 A | 8/1992 | Hollister |
| 5,151,089 A | 9/1992 | Kirk, III et al. |
| 5,154,285 A | 10/1992 | Hollister |
| 5,188,611 A | 2/1993 | Orgain |
| 5,197,954 A | 3/1993 | Cameron |
| RE34,252 E | 5/1993 | Pien |
| 5,207,653 A | 5/1993 | Janjua et al. |
| 5,232,454 A | 8/1993 | Hollister |
| 5,232,455 A | 8/1993 | Hollister |
| 5,242,417 A * | 9/1993 | Paudler ......................... 604/192 |
| 5,277,311 A | 1/1994 | Hollister |
| 5,312,369 A | 5/1994 | Arcusin et al. |
| 5,401,251 A | 3/1995 | Hui |
| 5,405,332 A | 4/1995 | Opalek |
| 5,423,765 A | 6/1995 | Hollister |
| 5,462,534 A | 10/1995 | Debreczeni |
| 5,485,854 A | 1/1996 | Hollister |
| 5,486,163 A | 1/1996 | Haynes |
| 5,490,841 A | 2/1996 | Landis |
| 5,509,907 A | 4/1996 | Bevilacqua |
| 5,533,984 A | 7/1996 | Parmigiani |
| 5,584,816 A | 12/1996 | Gyure et al. |
| 5,599,313 A | 2/1997 | Gyure et al. |
| 5,599,318 A | 2/1997 | Sweeney et al. |
| 5,603,699 A | 2/1997 | Shine |
| 5,632,732 A | 5/1997 | Szabo et al. |
| 5,643,219 A | 7/1997 | Burns |
| 5,662,617 A | 9/1997 | Odell et al. |
| 5,665,075 A | 9/1997 | Gyure et al. |
| 5,669,889 A | 9/1997 | Gyure et al. |
| 5,681,295 A * | 10/1997 | Gyure et al. .................. 604/263 |
| 5,693,022 A | 12/1997 | Haynes |
| 5,702,369 A | 12/1997 | Mercereau |
| 5,733,265 A | 3/1998 | Bachman et al. |
| 5,746,726 A | 5/1998 | Sweeney et al. |
| 5,807,351 A | 9/1998 | Kashmer |
| 5,836,920 A | 11/1998 | Robertson |
| 5,868,716 A | 2/1999 | Sweeney et al. |
| 5,876,831 A | 3/1999 | Rawal |
| 5,885,249 A | 3/1999 | Irisawa |
| 5,910,130 A | 6/1999 | Caizza et al. |
| 5,913,846 A | 6/1999 | Szabo |
| 5,993,426 A | 11/1999 | Hollister |
| 6,077,253 A | 6/2000 | Cosme |
| 6,080,137 A | 6/2000 | Pike |
| 6,120,482 A | 9/2000 | Szabo |
| 6,139,533 A | 10/2000 | Xia et al. |
| RE37,110 E | 3/2001 | Hollister |
| 6,319,232 B1 | 11/2001 | Kashmer |
| 6,328,713 B1 | 12/2001 | Hollister |
| 6,334,857 B1 | 1/2002 | Hollister et al. |
| 6,699,217 B2 | 3/2004 | Bennett et al. |
| 6,719,731 B2 * | 4/2004 | Parmigiani ..................... 604/192 |
| 2003/0181861 A1 * | 9/2003 | Wilkinson ..................... 604/192 |
| 2004/0215154 A1 | 10/2004 | Hwang et al. |
| 2005/0054986 A1 | 3/2005 | Simpson et al. |
| 2005/0065481 A1 | 3/2005 | Hauri et al. |
| 2005/0065482 A1 * | 3/2005 | Hauri et al. ................... 604/263 |
| 2005/0124944 A1 * | 6/2005 | Hwang ......................... 604/263 |

FOREIGN PATENT DOCUMENTS

| | | |
|---|---|---|
| GB | 2240273 A | 7/1991 |
| GB | 2240477 A | 8/1991 |
| WO | WO 87/07162 | 12/1987 |
| WO | WO 90/01348 | 2/1990 |
| WO | WO 91/09637 | 7/1991 |
| WO | WO 91/09638 | 7/1991 |
| WO | WO 91/09639 | 7/1991 |
| WO | WO 93/16745 | 9/1993 |

* cited by examiner

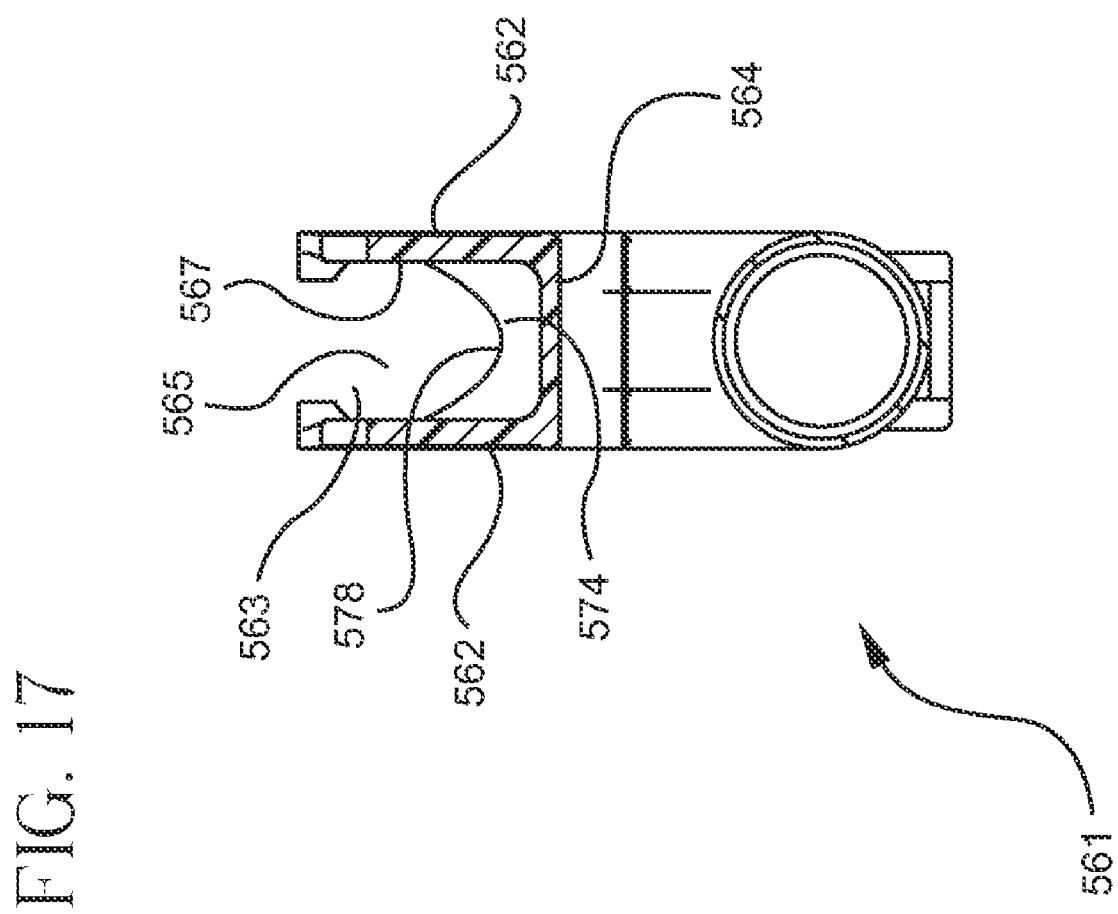

SYRINGE HAVING A HINGED NEEDLE SHIELD

FIELD OF THE INVENTION

The present invention relates generally to single use syringes having safety features and more specifically to a syringe having a hinged needle assembly and a hinged needle shield assembly for use with a syringe.

BACKGROUND OF THE INVENTION

Accidental needle sticks with new unused needle can cause injury and render the needle unfit for further use. Accidental needle sticks with a used needle can transmit disease. As a result, most prior art needle assemblies have a needle shield. Some prior art needle shields define a rigid sleeve that can be manually telescoped over a needle cannula. This procedure requires a healthcare worker to hold the syringe barrel in one hand and the shield in the other. Some medical procedures require the application of pressure to the penetration site after the needle has been removed. Thus, healthcare workers are often unable to use both hands for shielding the needle cannula. In these situations, workers merely deposit the used medical implement on a nearby surface with the intention of shielding at a more convenient time. However, until the needle is shielded or properly disposed of, it presents a potential danger to other people.

A needle shield which is hinged near the base of the needle has the advantage of allowing one handed needle reshielding. Thus providing the opportunity for reshielding, under most circumstances, immediately after use. Accordingly, a number of prior art needle shield assemblies have been developed that include such needle shields.

Various means have been provided for locking a hinged needle shield in the closed, needle protecting, position. Deflectable members have been provided in the needle shield for engaging the needle upon shielding and preventing subsequent unshielding of the needle. Such members trap the needle within the needle shield. Locking has also been accomplished by locking engagement of the needle shield with structure near the base of the needle.

Although hinged needle shields are known in the art, there is still a need for an improved hinged needle shield that is automatically locking, cost effective, easy to manufacture and having improved safety features.

SUMMARY OF THE INVENTION

A syringe assembly includes a syringe barrel having an elongate body defining a chamber for retaining fluid, an outside surface, and open proximal end and a distal end including a tip having a passageway therethrough in fluid communication with the chamber. Distal end further includes a barrel collar concentrically surrounding the tip. A needle assembly includes a needle cannula having a proximal end, a distal end and a lumen therethrough and a hub having an open proximal end including a cavity therein and a distal end attached to the proximal end of the needle cannula so that lumen of the needle cannula is in fluid communication with the cavity of the hub. The needle assembly is removably attached to the syringe barrel through frictional engagement of the cavity in the hub and the tip on the barrel. A plunger includes an elongate body portion having a proximal portion, a distal portion and a stopper slidably positioned in fluid tight engagement with the inside surface of the barrel for drawing fluid into and driving fluid out of the chamber by movement of the stopper relative to the barrel. The elongate body portion extends outwardly from the open end of the syringe barrel. A collar is rotatably connected to the outside surface of the barrel collar. An elongate needle shield is hingedly connected to the collar. The needle shield includes two side walls defining a longitudinal opening and a back wall between the side walls defining a recess having an interior surface. The needle shield is capable of pivoting from an open position wherein the needle cannula is exposed, to a close needle protecting position wherein the distal end of the needle cannula is within longitudinal opening of the shield. Structure for locking the needle shield in the closed needle protecting position when the needle shield is pivoted into the closed position is provided. The structure includes an arm projecting from the interior surface of the needle shield. The arm has a free end positioned so that when the needle shield is pivoted to the closed position, the needle cannula moves past the free end and is trapped in the needle shield by the arm. Structure for locking further includes a locking projection on the proximal end of the needle shield for lockingly engaging a ledge on the collar when the needle shield is pivoted to the closed position. A protuberance in the recess at the distal end of the needle shield is positioned to contact the hub when the needle shield is pivoted into the closed position to help prevent over-rotation of the needle shield past the needle protecting position. The tab on each of the side walls at the longitudinal opening of the needle shield is provided. The tabs have angled guide surfaces converging toward the longitudinal opening for guiding the needle cannula into the longitudinal opening when the needle shield is being pivoted to the closed position. Spring structure connects the collar and the needle shield for urging the needle shield toward the closed needle protecting position.

The syringe assembly may further include a rigid elongate needle cover having a distal end and an open proximal end and a side wall therebetween defining the receptacle. The needle covers removably engaged with the hub and contains needle cannula and is intended to protect the needle cannula before the syringe is used for injection and to prevent accidental positioning of the elongate needle shield in the closed position.

The protuberance in the recess of the needle shield can take other shapes such as a transverse rib extending between the side walls of the needle shield or a transverse rib having a transverse hub guiding surface.

The needle shield may contain two stiffening walls, each stiffening wall running parallel and outside of one of the side walls defining side channels outside of the longitudinal opening of the needle shield. With the needle shield having stiffening walls, the tabs may traverse the side channels to prevent the needle cannula from entering the side channels. A spring structure for urging the needle shield toward the closed position includes an over-center hinge which is substantially unbiased when the needle shield is in the open position.

The needle shield may be hingedly connected to the collar by a living hinge.

The syringe assembly may include spring means comprising an over-center hinge extending from the collar to the proximal end of the needle shield.

The needle shield, the collar, the living hinge and the over-center hinge may be a unitary structure integrally molded with thermoplastic material.

Locking projection on the needle shield may include two locking projections facing each other and projecting from the side walls of the needle shield into the recess.

The barrel collar of the syringe barrel may include an internal thread. The hub may include radial projections on its proximal end for engaging the internal thread of the barrel collar for holding the needle assembly securely to the barrel.

The stopper may be made of material selected from the list consisting of thermoplastic elastomers, natural rubber, synthetic rubber, thermoplastic materials and combinations thereof.

An alternative embodiment of the present invention includes a needle shield assembly for use with a barrel having an elongate body defining a chamber for retaining fluid, an outside surface, an open proximal and a distal end including a tip having a passageway therethrough in fluid communication with the chamber, and a barrel collar concentrically surrounding the barrel tip, a needle cannula having a proximal end, a distal end and a lumen therethrough, and a hub having an open proximal end including a cavity therein and a distal end attached to the proximal end of the cannula so that the lumen is in fluid communication with the cavity. The needle assembly is removable attached to the barrel through frictional engagement of the cavity in the hub and the tip on the barrel. The needle shield assembly comprises a collar rotatably connected to the outside surface of the barrel collar, an elongate needle shield is hingedly connected to the collar, the needle shield includes two side walls defining the longitudinal opening and a back wall between the side walls defining a recess having an interior surface. The needle shield is capable of pivoting from an open position wherein the needle cannula is exposed to the closed needle protecting position wherein the distal end needle cannula is within the longitudinal opening of the needle shield. Structure for locking the needle shield in the closed needle protecting position when the needle shield is pivoted into the closed needle protecting position includes an arm projecting from an interior surface of the needle shield. The arm includes a free end positioned so that when the needle shield is pivoted to the closed position, the needle cannula moves past the free end and is trapped in the needle shield by the arm. Structure for locking further includes a locking projection on the proximal end of the needle shield for locking engaging a ledge on the collar when the needle shield is pivoted to the closed position. A protuberance in the recess at the proximal end of the needle shield is positioned to contact the hub when the needle shield is pivoted in the closed position to help prevent over-rotation of the needle shield past the close needle protecting position. A tab on each of the side walls at the longitudinal opening is provided. Each tab includes an angled guide surface converging toward the longitudinal opening for guiding the needle into the longitudinal opening when the needle shield is being pivoted to the closed position. A spring connected to the collar and the needle shield is provided for urging the needle shield toward the closed needle protecting position.

BRIEF DESCRIPTION OF THE DRAWINGS

FIG. 17 is a cross-sectional view of another alternative embodiment of the elongate needle shield of the present invention. This embodiment includes a protuberance in the form of a transverse rib having a concave hub guiding surface.

DETAILED DESCRIPTION

Figure 1:
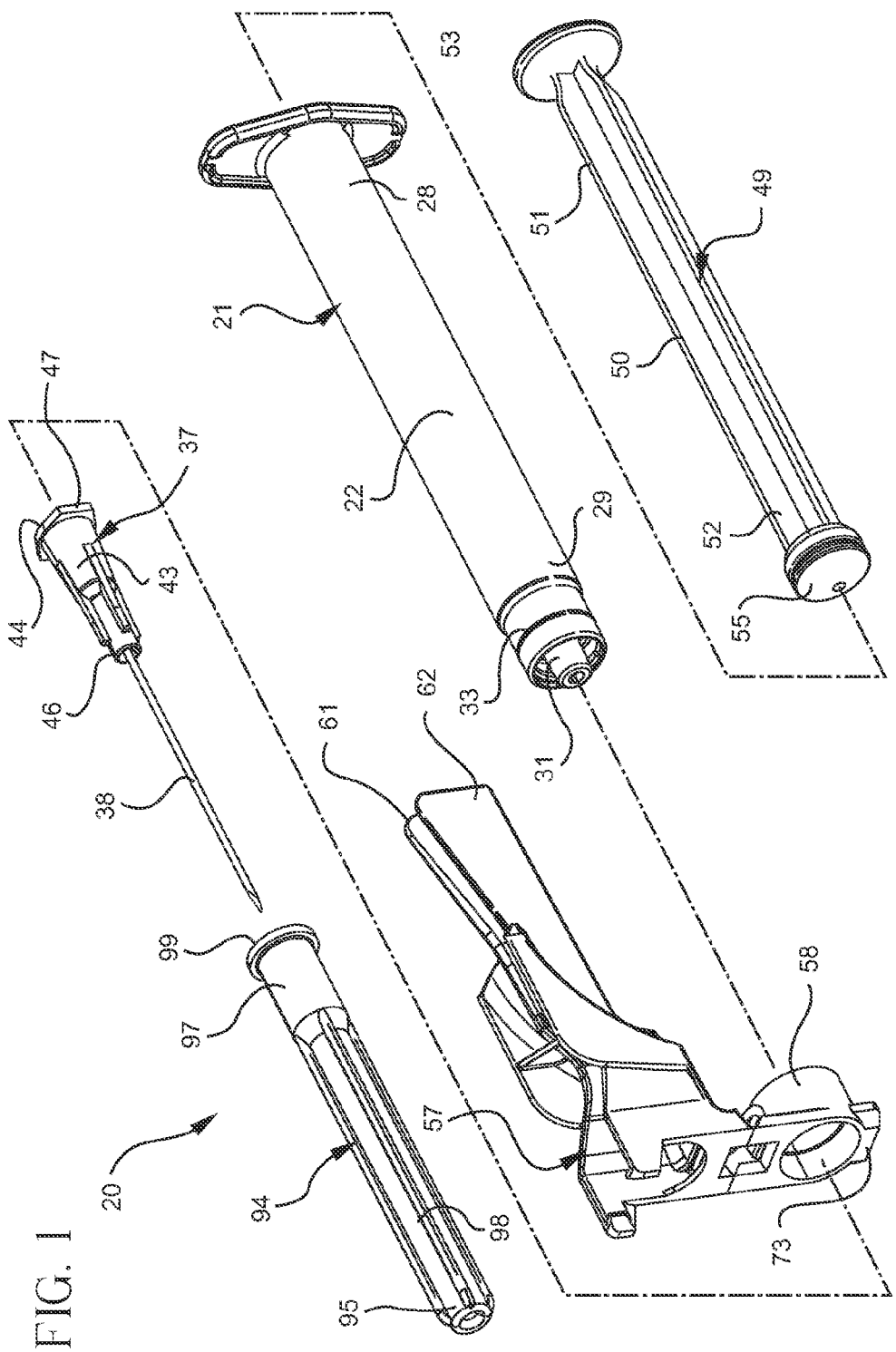
FIG. 1 is an exploded perspective view of the syringe assembly of the present invention.

While this invention is satisfied by embodiments in many different forms, there are shown in the drawings and will herein be described in detail, preferred embodiments of the invention with the understanding that the present disclosure is to be considered exemplary of the principles and are not intended to limit the invention to the embodiments illustrated. The scope of the invention will be measured by the appended claims and their equivalents.

Referring to FIGS. 1-11, a syringe assembly 20 of the present invention includes a syringe barrel 21 having an elongate body 22 defining a chamber 23 for retaining fluid 25, an outside surface 27 and open proximal end 28 and a distal end 29 including a tip 31 having a passageway therethrough in fluid communication with the chamber. The distal end of the barrel preferably includes a barrel collar 33 concentrically surrounding the tip.

A needle assembly 37 includes a needle cannula 38 having a proximal end 39 a distal end 40 and a lumen 41 therethrough and a hub 43. The hub includes an open proximal end 44 having a cavity 45 therein and a distal end 46 attached to the proximal end of the needle cannula so that the lumen is in fluid communication with the cavity. The needle assembly is removably attached to the barrel through frictional engagement of the cavity in the hub and the tip on the barrel.

The plunger 49 includes an elongate body portion 50 having a proximal portion 51, a distal portion 52 and a stopper 55 slidably positioned in fluid-tight engagement with the inside surface of the barrel for drawing fluid into and driving fluid out of the barrel chamber by movement of the stopper relative to the barrel. The elongate body portion extends outwardly from the open end of the barrel.

A needle shield assembly 57 includes a collar 58 rotatably connected to the outside surface of the barrel collar and hingedly connected to an elongate needle shield 61. The needle shield includes two side walls 62 defining a longitudinal opening 63 and a back wall 64 between the side walls defining a recess 65 having an interior surface 67. The needle shield in this embodiment is connected to the collar through a living hinge 81. The needle shield is capable of pivoting from an open position wherein the needle cannula is exposed, as best illustrated in FIGS. 2-5, to a closed needle protecting position wherein the distal end of the needle cannula is within the longitudinal opening of the shield.

Structure for automatically locking the needle shield in the needle protecting position when the needle shield is pivoted into the needle shielding position includes, in this embodiment, at least one arm 69 projecting from the interior surface of the needle shield. The arm includes a free end 70 positioned so that when the needle shield is pivoted to the close position, the needle cannula moves past the free end of the arm and is trapped in the needle shield by the arm. Structure for automatically locking the needle shield in the closed needle protecting position further includes a locking projection on the proximal end of needle shield. In this embodiment, there are two locking projections 71 on the proximal end of the needle shield for lockingly engaging a ledge 73 on the collar when the needle shield is pivoted into the closed needle protecting position.

Figure 2:
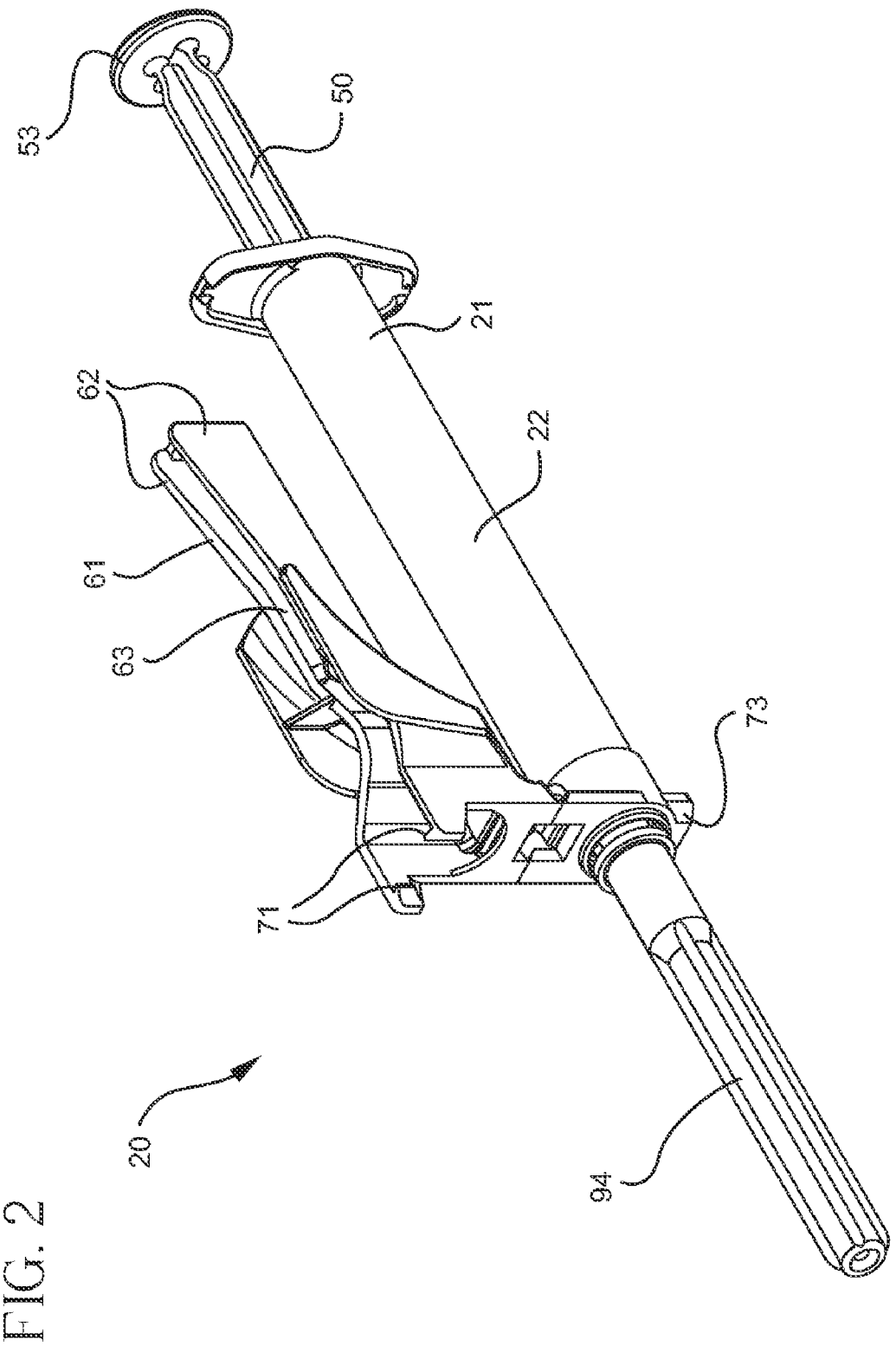
FIG. 2 is a perspective view of the syringe assembly of the present invention.

A rigid elongate needle cover 94 includes a distal end 95, an open proximal end 97 and a side wall therebetween defining a receptacle 99 in the needle cover. Before use, as illustrated in FIG. 2, needle cover 94 is removably engaged to hub 43 with needle cannula 38 in the needle cover receptacle. Preferably, the syringe assembly is sterilized in a protective package with the needle cover in place. The needle cover provides a contamination barrier for the needle after the syringe assembly is removed from the sterile package. Accordingly, the user is assured of a clean needle at the time of first use. At the time of first use, the needle cover is removed by overcoming the engagement forces between the hub and the open proximal end of the needle cover. The needle cover also provides an advantage in that while it is in position on the hub, the needle shield cannot be rotated into the closed needle protecting position.

Figure 9:
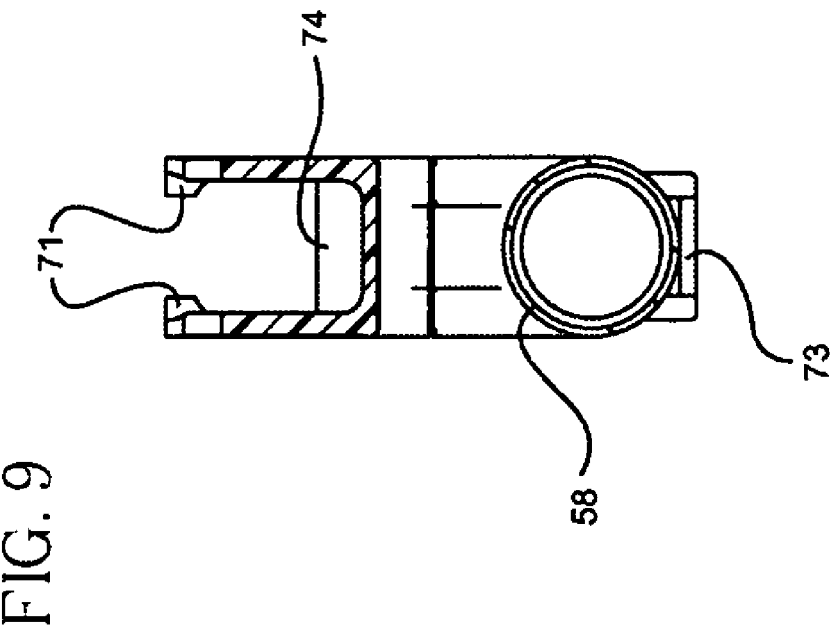
FIG. 9 is a cross-sectional view of the needle shield of FIG. 7 taken along line 9-9.
Figure 8:
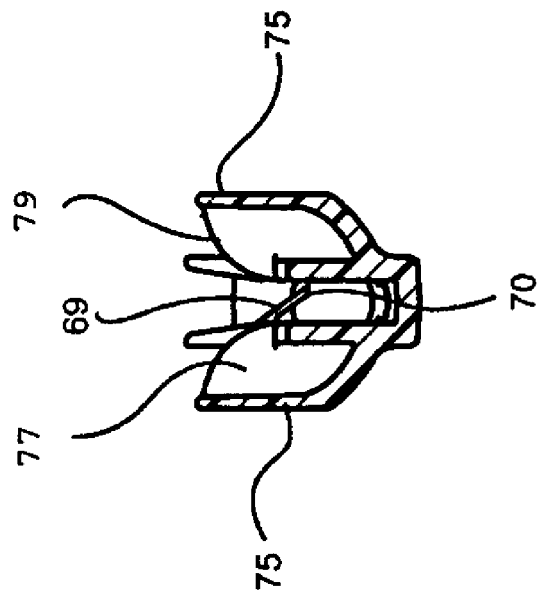
FIG. 8 is a cross-sectional view of the needle shield of FIG. 7 taken along line 8-8.
Figure 11:
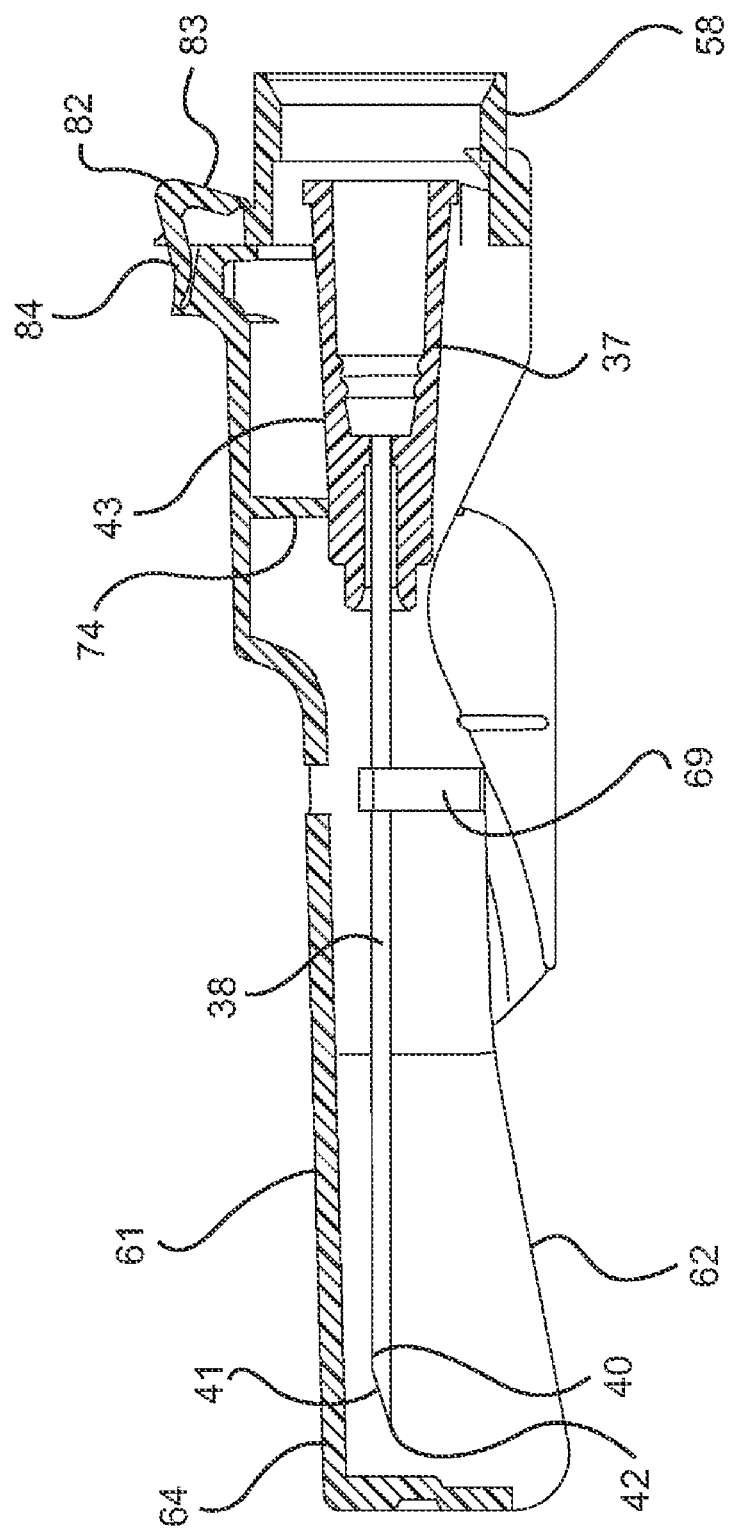
FIG. 11 is a cross-sectional view of the syringe assembly of FIG. 10 taken along line 11-11.

A protuberance in the recess of the needle shield at the proximal end of the needle shield is positioned to contact the hub when the needle shield is pivoted into the closed needle protecting position to help prevent over-rotation of the needle shield past the needle protecting position. In this embodiment, the protuberance is a transverse rib 74 extending between side walls 62 of the needle shield, as illustrated in FIG. 9. It is an important feature of the present invention that the needle shield is structured to prevent over-rotation of the needle shield as it is pivoted into the closed needle protecting position. As can be seen in FIG. 11 transverse rib 74 contacts needle hub 43 to resist over-rotation. Over-rotation can cause the needle shield to contact the needle cannula and bend the needle cannula if excessive force is used. When excessive force is discontinued, the needle shield will relax to its normal position with the sharp end of the needle close to or extending outwardly from the longitudinal opening of the needle shield so that it is no longer adequately protected by the needle shield.

The needle shield in this embodiment preferably, but not necessarily, includes two stiffening walls 75 which enhance the rigidity of the needle shield. Each stiffening wall 75 runs parallel and outside of one of the side walls 62 defining side channels 76 outside of the longitudinal opening of the needle shield. The extra width of the needle shield in the area of the stiffening walls provides a larger contact surface for the user to apply digital force when pivoting the needle shield to the closed position.

A tab 77 is connected to each of the side walls 62 at the longitudinal opening of the needle shield. The tabs have angled guide surfaces 79 converging toward longitudinal opening 63 of the needle shield for guiding the needle cannula into the longitudinal opening when the needle shield is being pivoted to the closed needle protecting position. Tabs having angled guide surfaces are an important feature of the present invention since they help guide the needle into the recess of the needle shield thus helping to prevent the needle from being outside of the recess when the needle shield is in the closed needle protection position. In this embodiment, tabs also prevent the needle from entering the side channels when the needle shield is being pivoted into the closed position.

Figure 3:
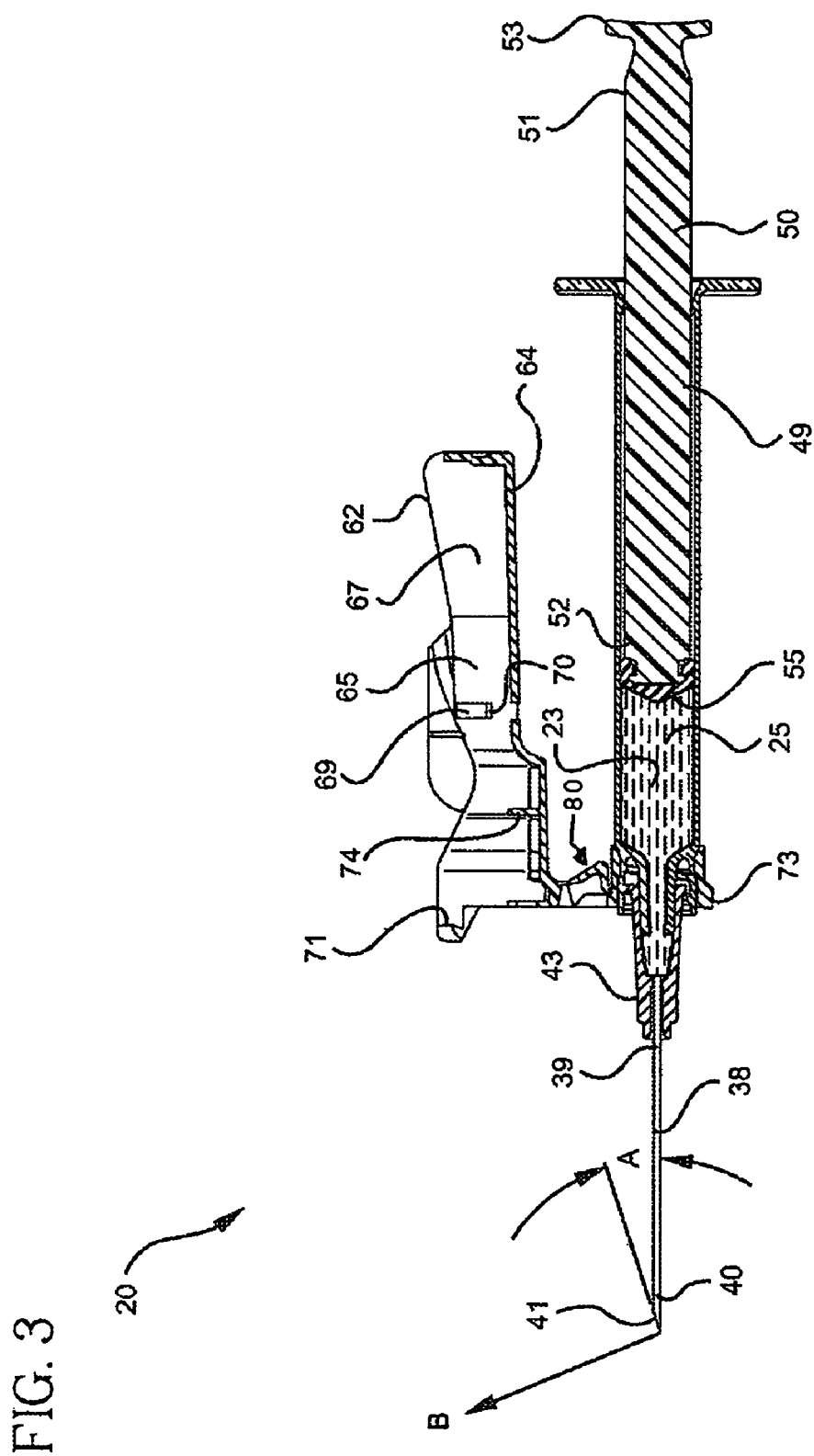
FIG. 3 is a cross-sectional side elevational view of the syringe assembly of the present invention with the plunger in position to perform an injection.

As best illustrated in FIG. 3, sharpened tip 42 of needle cannula 38 is sharpened to a bevel shape having a bevel surface 48 oriented at angle A with respect to the longitudinal axis of the needle cannula. Bevel surface 48 faces direction B. The rotational connection of the collar to the barrel collar is an important feature of the present invention because it allows rotation of the needle shield around the barrel so that the bevel surface faces the side of the barrel where the needle shield is located. Rotation of the needle shield to this position makes it easier to insert the needle into a patient's vein. Accordingly, it is desirable to have bevel surface 48 facing the same side of the needle assembly as the needle shield when the needle shield is in the open position, so that the needle shield does not interfere with the positioning of the syringe close to the patient's body, for example, the patient's arm, when attempting to gain access into a vein.

The needle shield assembly also includes an over-center hinge assembly 80 connected to collar 58 and needle shield 61 for allowing the needle shield to pivot to the closed needle protecting position and for urging the needle shield toward the closed needle protecting position. Specifically, a hinge which in this embodiment is a living hinge 81, hingedly connects the collar to the needle shield. Hinge 81 is a substantially nonbiasing hinge member which defines rotational path of the needle shield from the open position through the closed needle protecting position. Hinge 81 in combination with spring element 82 forms the over-center hinge assembly. Spring element 82 in this preferred embodiment includes a first segment 83 and a second segment 84 orthogonally aligned to one and other in an unbiased condition as illustrated in FIGS. 3-6. However, first and second segments 83 and 84 of spring element 82 can be resiliently deflected from the unbiased angled alignment into a more linear alignment. Rotation of the needle shield from the open position toward the closed position will cause segments 83 and 84 to be deflected from the right angle condition shown in FIGS. 3-6 towards a more linear orientation. The user of the syringe assembly must manually overcome the forces attributable to the resiliency of spring element 82 to move the needle shield to an intermediate position between the open position and the closed position. The resiliency inherent in spring element 82 will urge the spring segment back toward an undeflected right angle condition. This resiliency will effectively propel the needle shield toward the closed needle protecting position. The self-propelling attributes of the over-center hinge are desirable to facilitate one-hand shielding of the needle. Also important is the fact that spring element 82 is in a stable condition in the orientation illustrated in FIGS. 3-6 with virtually no stored energy exerting pressure on the plastic components of the needle shield assembly. Stored energy acting on plastic can affect the reliability and performance of the part. In this instance, however, the stored energy is accumulated only after the needle shield is rotated from the open position toward the closed position. The accumulated energy then performs work for the user by urging the needle shield toward the closed needle protecting position of FIG. 11. Spring element 82 will, preferably, be stable with, preferably, little or no stored energy while in the closed position illustrated in FIG. 11. In this embodiment, the needle shield, the collar, the living hinge and the spring element are a unitary structure integrally molded of thermoplastic material.

It is unfortunate that sometimes the people who most need the benefit of a syringe assembly with needle protecting features are the least able to afford such protection. This is especially true for mass immunization programs in underdeveloped countries. Lower priced products allow more products to be purchased for these programs. The needle shield assembly of the present invention having a transverse rib to prevent over-rotation and tabs with angled guide surfaces to guide the needle into the needle cannula into the recess of the needle shield allow the needle shield assembly to be made with less plastic at a correspondingly lower price since the plastic material is the major determiner of high volume product price. In using less plastic the needle shield assembly can be less rigid and more likely to deflect if the user applies excessive digital pressure to the needle shield to rotate it into the closed position. This digital pressure can cause the needle shield and/or the hinge between the needle shield and the collar to deflect left or right wherein the needle could avoid the cavity in the shield and/or to over-rotate and deflect the shield which can bend the needle causing it to protrude out of the longitudinal opening of the needle shield. The tabs with angled guide surfaces compensates for left and right deflection and the transverse rib compensates for possible over-rotation while moving the needle shield through the closed position. Accordingly, a needle shield having the inventive features of present embodiment can be made using less plastic material and sold for less money, allowing more people to benefit from the safety features of the needle shield assembly than otherwise would be possible.

It is preferred that the barrel collar include an internal thread 34 and the hub include radial projections 47 on its proximal end for engaging thread 34 for holding the needle assembly securely to the barrel. To attach the needle assembly to the barrel with these new elements, the user places the needle hub cavity over the barrel tip so that radial projections 47 on the hub engage thread 34 in the barrel collar. The needle assembly then rotated or screwed into the locking collar so that the needle assembly is held tightly on the distal end of the syringe barrel through interaction of the thread and the projections and a frictional interference between tip 31 on the barrel and cavity 45 and the hub. It is within the purview of the present invention to include a needle assembly having one-piece construction where the barrel and the hub are formed of one piece and the needle cannula is attached directly to the hub portion of the barrel without the use of a removable hub.

It is preferred but not necessary that the stopper be a separate element attached to the elongate body portion of the plunger and that it is made of material selected from the list consisting of thermoplastic elastomers, natural rubber, synthetic rubber, thermoplastic materials and combinations thereof. It is also within the purview of the present invention to have a one-piece plunger where the stopper and the plunger rod and integrally formed.

Figure 4:
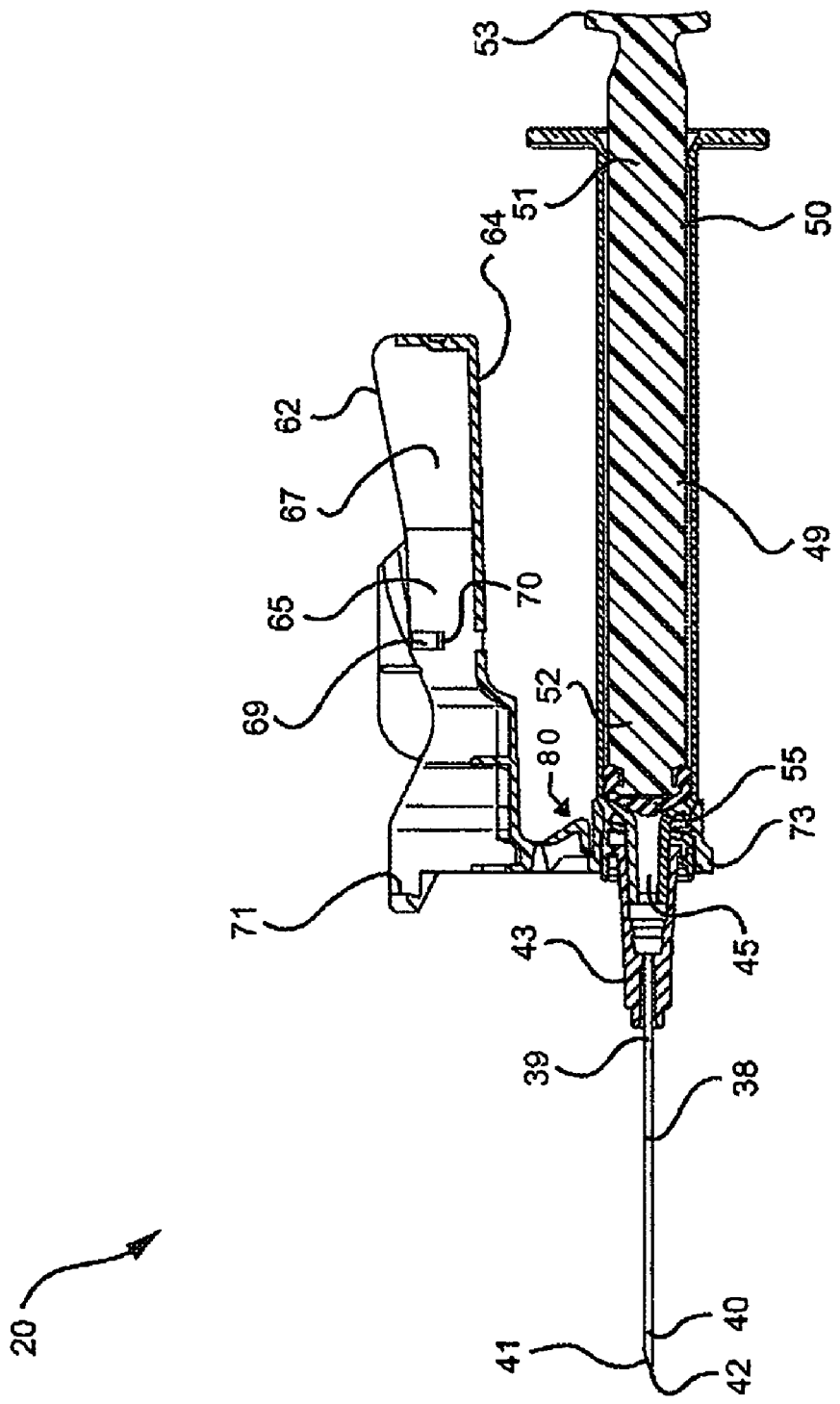
FIG. 4 is a cross-sectional side elevational view of the syringe assembly of FIG. 3 with the plunger in the position after an injection has been performed.
Figure 5:
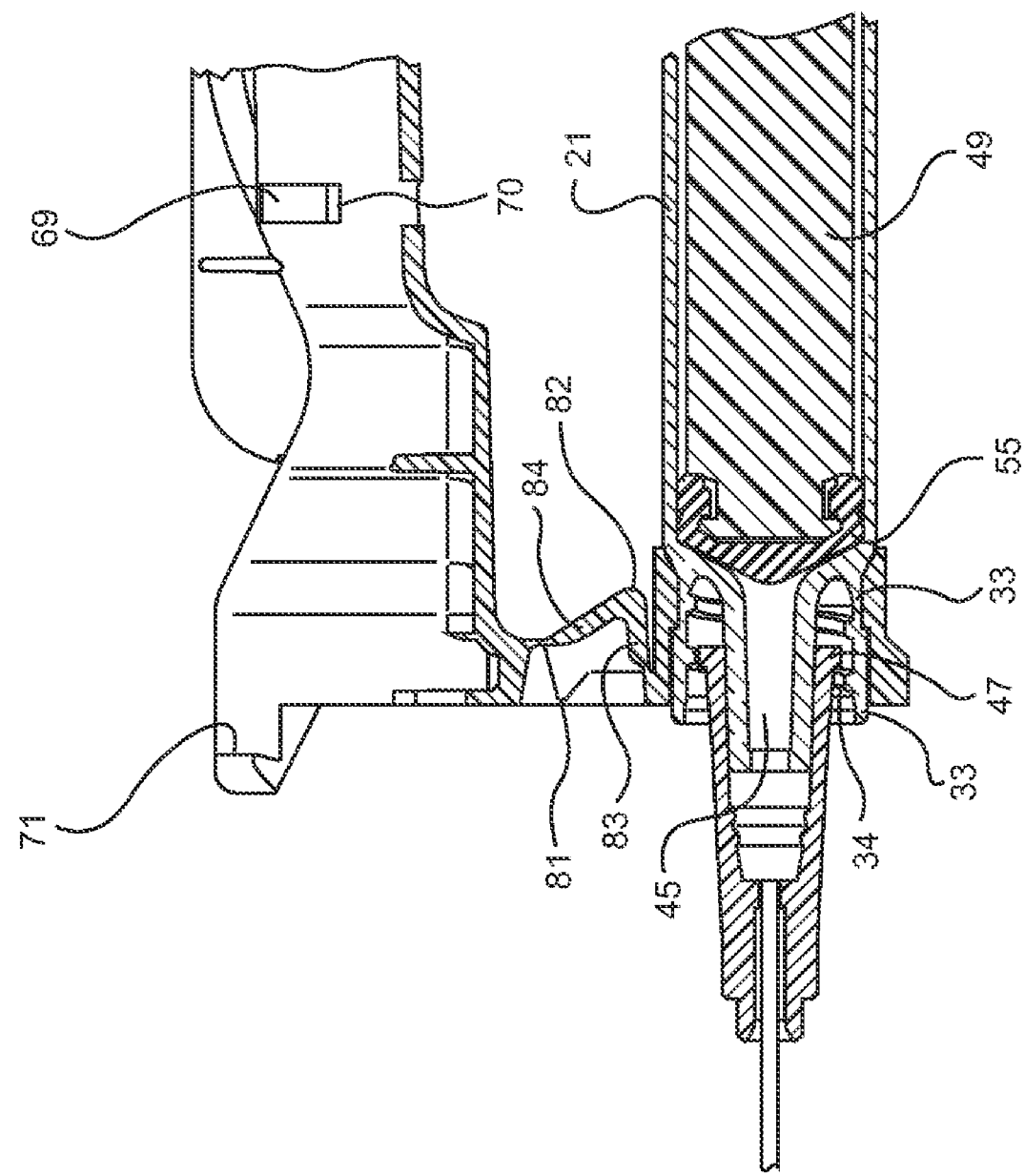
FIG. 5 is an enlarge cross-sectional side elevation view of the distal end of the syringe assembly of FIG. 4.
Figure 6:
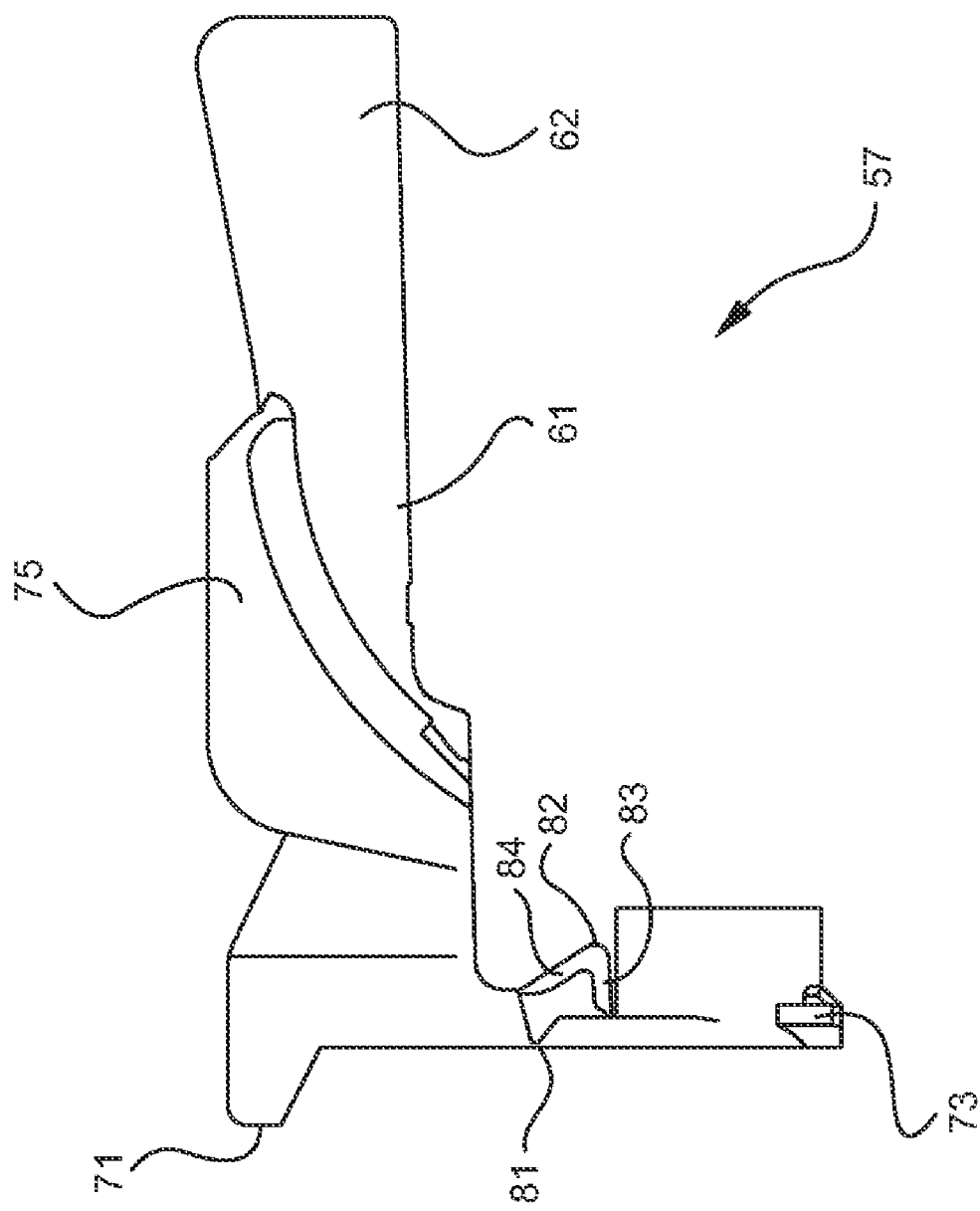
FIG. 6 the side elevational view of the needle shield assembly of the present invention.
Figure 7:
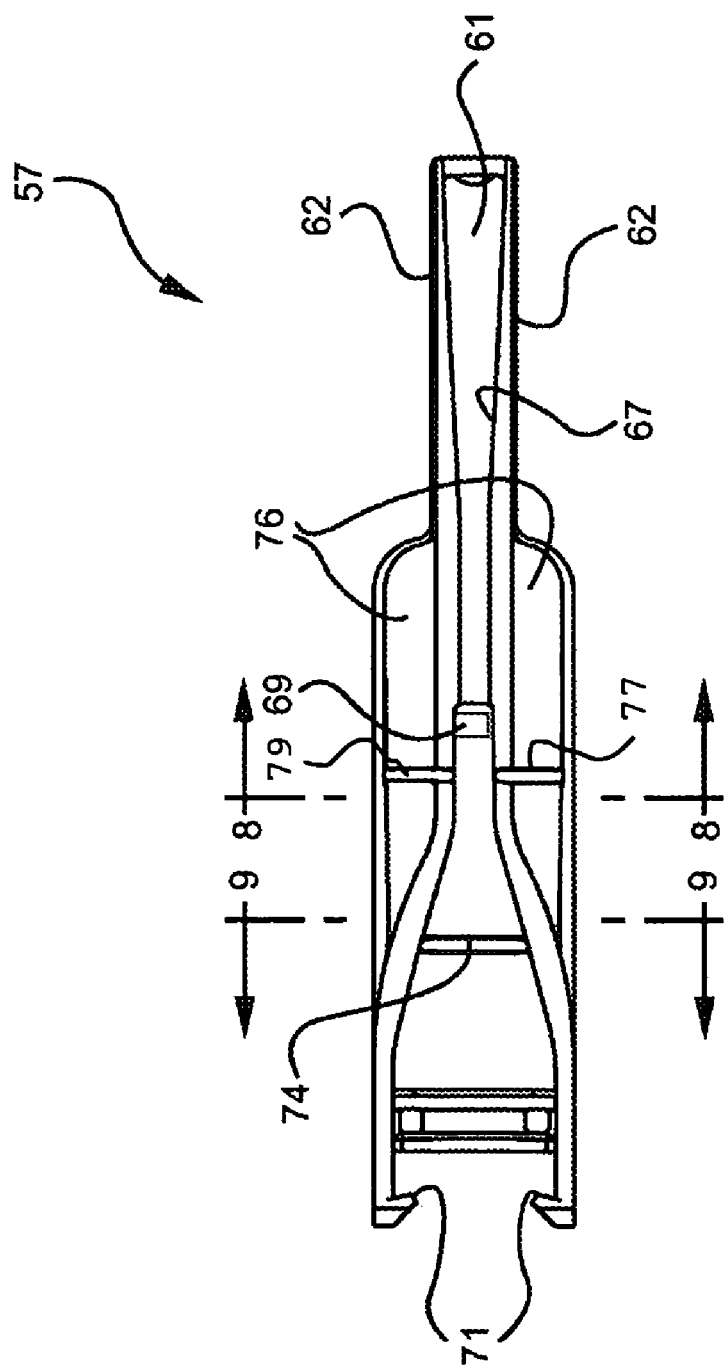
FIG. 7 is a bottom plan view of the elongate needle shield of FIG. 6.
Figure 10:
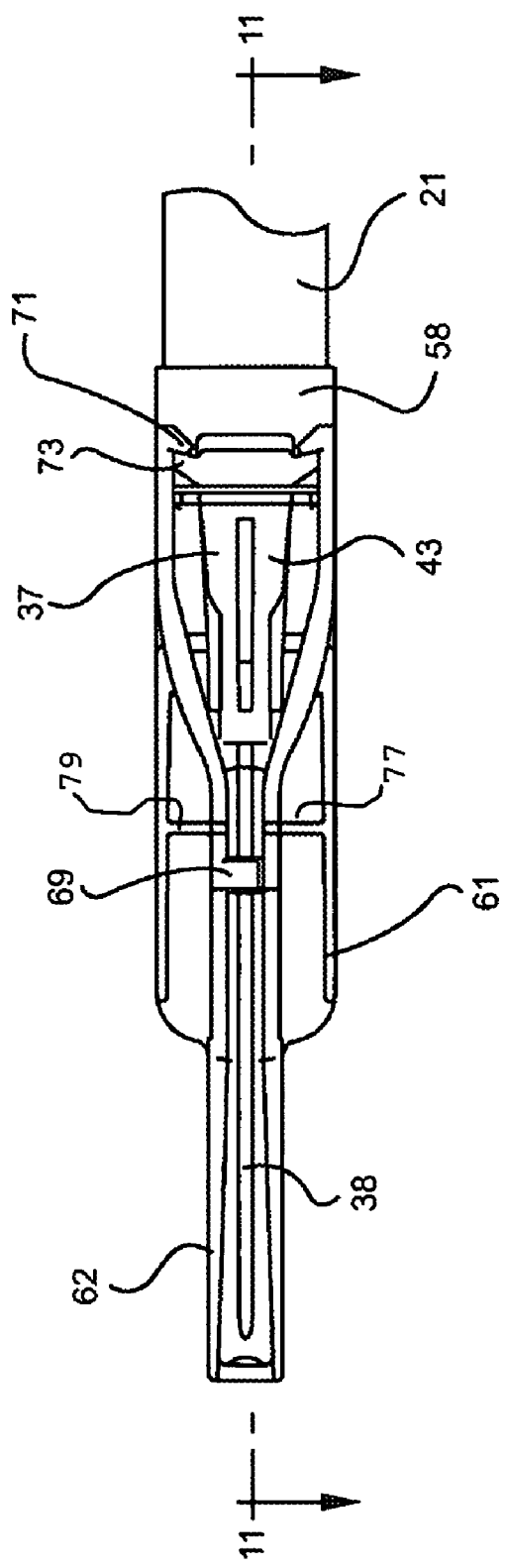
FIG. 10 is a bottom plan view of the syringe assembly of the present invention showing the needle shield in the closed needle protecting position.

In operation, the syringe assembly can be filled from a vial ampule or other suitable container using known safe procedures. The syringe is filled by inserting the needle cannula into a vial and withdrawing plunger 49. This will cause liquid to be drawn the lumen of the needle cannula and into chamber 23 and best illustrated in FIG. 3. Fluid 25 in chamber 23 can now be injected into a patient or delivered in another suitable manner such as through the pierceable septum of a catheter connector. This occurs by applying axial force to the thumb-press 53 to cause plunger 49 to advance within the barrel thereby expelling fluids through the lumen of the needle cannula. At the completion of the injection process, the plunger is positioned as illustrated in FIGS. 4-5. The user can then, using one hand, grasp the syringe barrel and apply digital force, such as through the thumb, to rotate the needle shield from the open position through an intermediate position wherein the over-center hinge is energized and the needle shield will advance towards the closed needle protecting position. Additional force may be necessary for the user to lock the needle shield in the closed needle protecting position. In this position, the needle cannula is held in the shield by arm 69 and the needle shield is locked in the closed position through the action of the engagement of locking projections 71 on the needle shield and ledge 73 on the collar, as illustrated in FIGS. 10 and 11.

Figure 12:
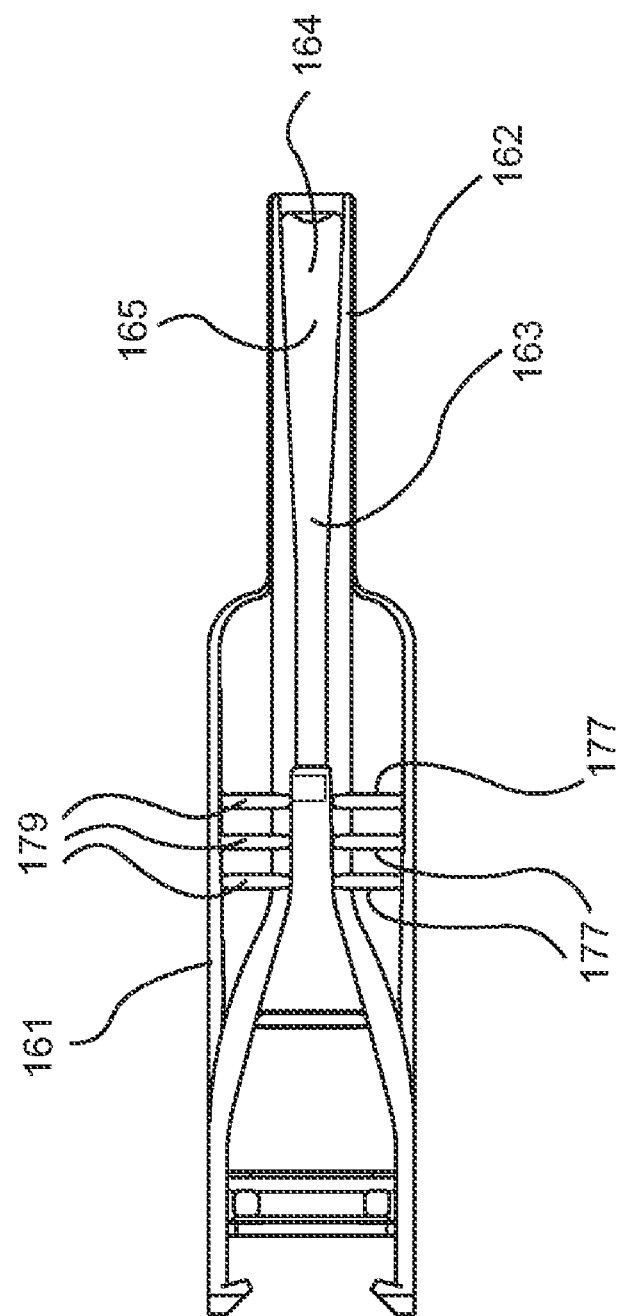
FIG. 12 is a bottom plan view of an alternative needle shield assembly of the present invention.

FIG. 12 illustrates an alternative embodiment of the present invention. This embodiment functions substantially similar to the embodiment of FIGS. 1-11. In this alternative embodiment, needle shield assembly 157 includes an elongate needle shield 161 hingedly connected to a collar. The needle shield includes two side walls 162 defining a longitudinal opening 163 and a back wall 164 between the side walls defining a recess 165. A plurality of tabs, in this case six tabs 177, having guide surfaces 179 converging toward longitudinal opening 163 of the needle shield for guiding the needle cannula into the longitudinal opening when the needle shield is being pivoted to the closed needle protecting position.

Figure 13:
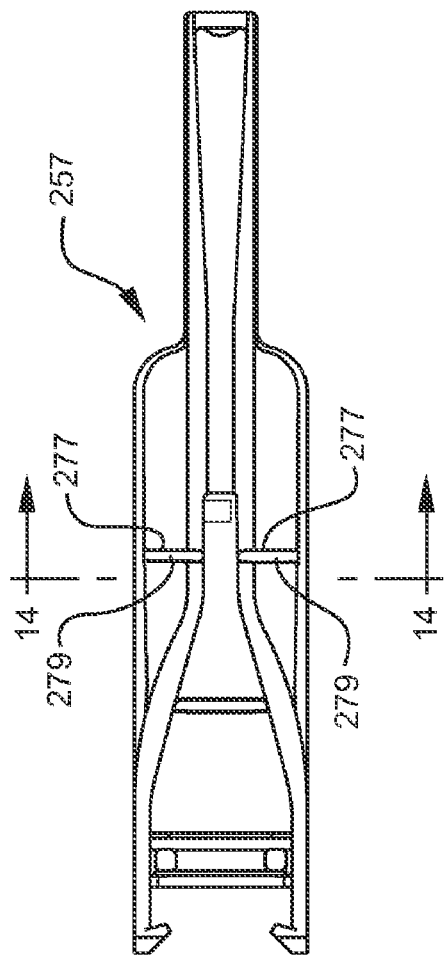
FIG. 13 is a bottom plan view of another alternative embodiment of the needle shield assembly of the present invention.
Figure 14:
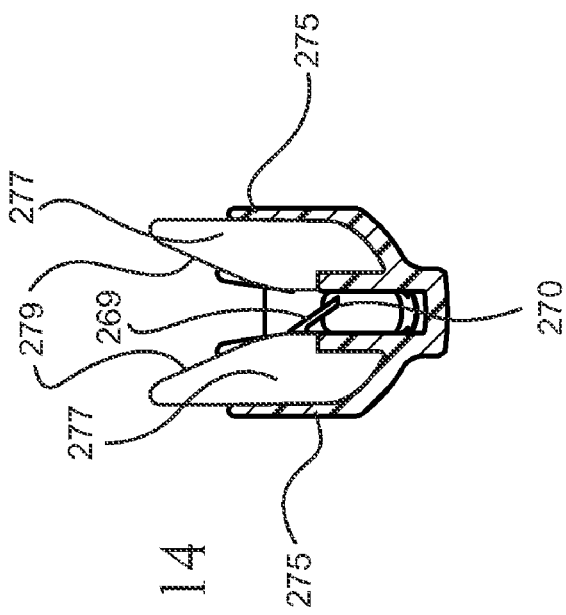
FIG. 14 is a cross-sectional view of the needle shield assembly FIG. 13 taken along line 14-14.

FIGS. 13 and 14 illustrate another alternative embodiment of the present invention. This embodiment functions substantially similar to the embodiment of FIGS. 1-11. In this alternative embodiment, needle shield assembly 257 includes an elongate needle shield 261 hingedly connected to a collar. The needle shield includes two side walls 262 defining a longitudinal opening 263 and a back wall 264 between the side walls defining a recess 265. A plurality of tabs, in this case two tabs 277, having guide surfaces 279 converging toward longitudinal openings 263 of the needle shield for guiding the needle cannula into the longitudinal opening when the needle shield is being pivoted to the closed needle protecting position. In this embodiment, the tabs extend outwardly beyond the side channels creating longer guide surfaces 279 to contain the needle sooner and provide a shallower angle for the guide surface to less abruptly guide the needle cannula toward the recess.

Figure 15:
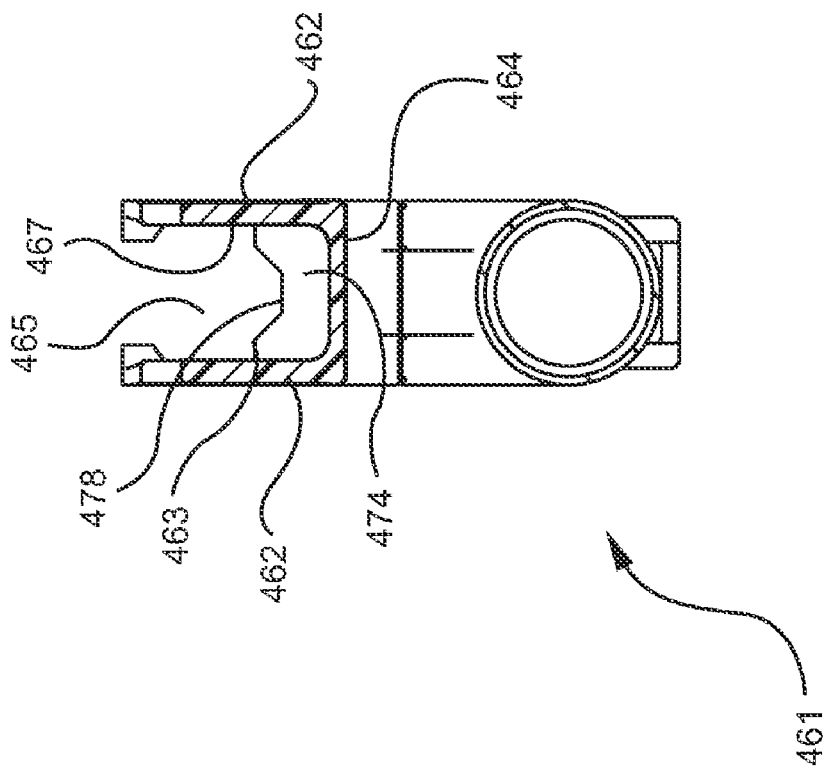
FIG. 15 is cross-sectional view of an alternative embodiment of the elongate needle shield having a protuberance in the shape of a tapered boss.

FIG. 15 illustrates an alternative embodiment of the elongate needle shield of the present invention. In this embodiment, an elongate needle shield 361 includes two side walls 362 defining a longitudinal opening 363 and a back wall 364 between the side walls defining a recess 365 having an interior surface 367. A protuberance 374 in the form of a tapered boss projects from interior surface 367 and is positioned to contact the hub when the needle shield is pivoted into the closed needle protecting position to help prevent over-rotation of the needle shield past the needle protecting position.

Figure 16:
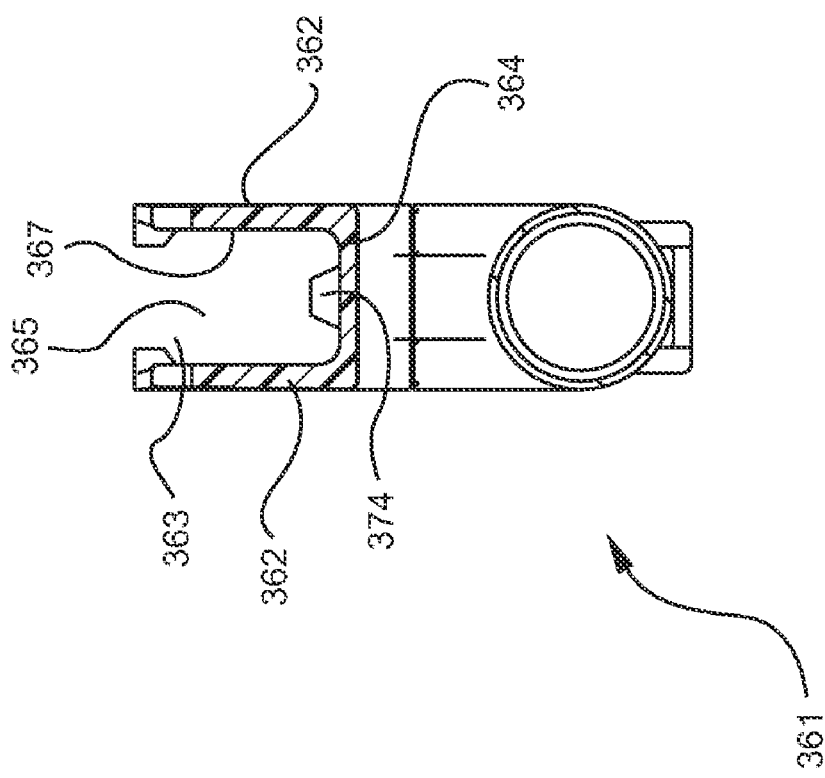
FIG. 16 is a cross-sectional view of another alternative embodiment of the elongate needle shield of the present invention. This embodiment includes a protuberance in the form of a transverse rib with a concave needle hub holding portion.

FIG. 16 illustrates another alternative embodiment of the elongate needle shield of the present invention. In this embodiment, an elongate needle shield 461 includes two side walls 462 defining a longitudinal opening 463 and a back wall 464 between the side walls defining a recess 465 having an interior surface 467. A protuberance in the form of a transverse rib 474 having a hub receiving recess 478 projects from interior surface 467 and is positioned to contact the hub when the needle shield is pivoted into the closed needle protecting position to help prevent over-rotation of the needle shield past the needle protecting position.

FIG. 17 illustrates another alternative embodiment of the elongate needle shield of the present invention. In this embodiment, an elongate needle shield 561 includes two side walls 562 defining a longitudinal opening 563 and a back wall 564 between the side walls defining a recess 565 having an interior surface 567. A protuberance in the form of a transverse rib 574 having a concave hub guiding surface 578 projects from interior surface 567 and is positioned to contact the hub when the needle shield is pivoted into the closed needle protecting position to help prevent over-rotation of the needle shield past the needle protecting position. The concave hub guiding surface is very desirable since it helps compensate for excessive force applied to the needle shield which can misalign recess 565 in the needle shield with respect to the needle cannula. Specifically, the concave hub guiding surface of a misaligned needle shield will contact the hub earlier in the needle shield's rotation into the closed position, to help guide the needle shield toward a central position wherein the needle cannula enters more toward the center of recess 565 than with a straight transverse rib.

What is claimed is:

1. A syringe assembly comprising:
    a syringe barrel having an elongate body defining a chamber for retaining fluid, an outside surface, an open proximal end and a distal end including a tip having a passageway therethrough in fluid communication with said chamber, said distal end further including a barrel collar concentrically surrounding said tip;
    a needle assembly including a needle cannula having a proximal end, a distal end and a lumen therethrough, and a hub having an open proximal end including a cavity therein and a distal end attached to said proximal end of said needle cannula so that said lumen is in fluid communication with said cavity, said needle assembly being removably attached to said barrel through frictional engagement of said cavity in said hub and said tip;
    a plunger including an elongate body portion having a proximal portion, a distal portion and a stopper slidably positioned in fluid-tight engagement with said inside surface of said barrel for drawing fluid into and driving fluid out of said chamber by movement of said stopper relative to said barrel, said elongate body portion extending outwardly from said open proximal end of said barrel;
    a collar rotatably connected to said outside surface at said barrel collar;
    an elongate needle shield hingedly connected to said collar, said needle shield having two side walls defining a longitudinal opening and a back wall between said side walls defining a recess having an interior surface, said needle shield capable of pivoting from an open position wherein said needle cannula is exposed, to a closed needle protecting position wherein said distal end of said needle cannula is within said longitudinal opening of said shield;
    two stiffening walls, each stiffening wall having a distal end and a proximal end and running parallel and outside of one of said side walls defining side channels outside of said longitudinal opening of said needle shield;
    means for locking said needle shield in said needle protecting position when said needle shield is pivoted into said needle protecting position including an arm projecting from said interior surface of said needle shield, said arm having a free end positioned so that when said needle shield is pivoted to said closed position, said needle cannula moves past said free end and is trapped in said needle shield by said arm, said means for locking further including a locking projection on said proximal end of said needle shield for lockingly engaging a ledge on said collar when said needle shield is pivoted into said closed position;
    a protuberance in said recess at said proximal end of said needle shield positioned to contact said hub when said needle shield is pivoted into said needle protecting position to help prevent over-rotation of said needle shield past said needle protecting position;
    a tab on each side of said side walls at said longitudinal opening, said tabs traversing said side channels between the distal end and the proximal end of each stiffening wall to prevent said needle cannula from entering said side channels and having angled guide surfaces converging toward said longitudinal opening for guiding said needle cannula into said longitudinal opening when said needle shield is being pivoted to said needle protecting position; and
    spring means connected to said collar and said needle shield for urging said needle shield toward said needle protecting position.

2. The syringe assembly of claim 1 further including a rigid elongate needle cover having a distal end and an open proximal end and a sidewall therebetween defining a receptacle, said needle cover removably engaging said hub and containing said needle cannula in said receptacle.

3. The syringe assembly of claim 1 wherein said protuberance is a transverse rib extending between said two side walls of said needle shield.

4. The syringe assembly of claim 1 wherein said protuberance is a transverse rib having a concave hub guiding surface.

5. The syringe assembly of claim 1 wherein said spring means is substantially unbiased when said needle shield is in said open position.

6. The syringe assembly of claim 1 wherein said needle shield is hingedly connected to said collar by a living hinge.

7. The syringe assembly of claim 6 wherein said spring means comprises an over-center hinge extending from said collar to said proximal end of said needle shield.

8. The syringe assembly of claim 7 wherein said needle shield, said collar, said living hinge and said over-center hinge are a unitary structure integrally molded of thermoplastic material.

9. The syringe assembly of claim 1 wherein said locking projection includes two locking projections facing each other and projecting from said side walls into said recess.

10. The syringe assembly of claim 1 wherein said barrel collar includes an internal thread.

11. The syringe assembly of claim 10 wherein said hub includes radial projections on its proximal end for engaging said thread for holding said needle assembly securely to said barrel.

12. The syringe assembly of claim 1 wherein said stopper is made of material selected from the list consisting of thermoplastic elastomers, natural rubber, synthetic rubber, thermoplastic materials and combinations thereof.

13. A needle shield assembly for use with a barrel having an elongate body defining a chamber for retaining fluid, an outside surface, an open proximal end and a distal end including a tip having a passageway therethrough in fluid communication with said chamber, said distal end further including a barrel collar concentrically surrounding said tip and a needle assembly including a needle cannula having a proximal end, a distal end and a lumen therethrough, and a hub having an open proximal end including a cavity therein and a distal end attached to said proximal end of said needle cannula so that said lumen is in fluid communication with said cavity, said needle assembly being removably attached to said barrel through frictional engagement of said cavity in said hub and said tip comprising;

a collar rotatably connected to said outside surface at said barrel collar;

an elongate needle shield hingedly connected to said collar, said needle shield having two side walls defining a longitudinal opening and a back wall between said side walls defining a recess having an interior surface, said needle shield capable of pivoting from an open position wherein said needle cannula is exposed, to a closed needle protecting position wherein said distal end of said needle cannula is within said longitudinal opening of said shield;

two stiffening walls, each stiffening wall having a distal end and a proximal end and running parallel and outside of one of said side walls defining side channels outside of said longitudinal opening of said needle shield;

means for locking said needle shield in said needle protecting position when said needle shield is pivoted into said needle protecting position including an arm projecting from said interior surface of said needle shield, said arm having a free end positioned so that when said needle shield is pivoted to said closed position, said needle cannula moves past said free end and is trapped in said needle shield by said arm, said means for locking further including a locking projection on said proximal end of said needle shield for lockingly engaging a ledge on said collar when said needle shield is pivoted into said closed position;

a protuberance in said recess at said proximal end of said needle shield positioned to contact said hub when said needle shield is pivoted into said needle protecting position to help prevent over-rotation of said needle shield past said needle protecting position;

a tab on each side of said side walls at said longitudinal opening, said tabs traversing said side channels between the distal end and the proximal end of each stiffening wall to prevent said needle cannula from entering said side channels and having angled guide surfaces converging toward said longitudinal opening for guiding said needle cannula into said longitudinal opening when said needle shield is being pivoted to said needle protecting position; and spring means connected to said collar and said needle shield for urging said needle shield toward said needle protecting position.

14. The needle shield assembly of claim 13 wherein said protuberance is a transverse rib extending between said two side walls of said needle shield.

15. The needle shield assembly of claim 13 wherein said protuberance is a transverse rib having a concave hub guiding surface.

16. The needle shield assembly of claim 13 wherein said spring means is substantially unbiased when said needle shield is in said open position.

17. The needle shield assembly of claim 13 wherein said needle shield is hingedly connected to said collar by a living hinge.

18. The needle shield assembly of claim 17 wherein said spring means comprises an over-center hinge extending from said collar to said proximal end of said needle shield.

19. The needle shield assembly of claim 18 wherein said needle shield, said collar, said living hinge and said over-center hinge are a unitary structure integrally molded of thermoplastic material.

20. The needle shield assembly of claim 13 wherein said locking projection includes two locking projections facing each other and projecting from said side walls into said recess.

\* \* \* \* \*